United States Patent
Sekiguchi et al.

(10) Patent No.: US 9,156,751 B2
(45) Date of Patent: Oct. 13, 2015

(54) LUBRICATING OIL COMPOSITION AND LUBRICATING OIL COMPOSITION FOR CONTINUOUSLY VARIABLE TRANSMISSION

(75) Inventors: Hiroki Sekiguchi, Sodegaura (JP);
Toshiyuki Tsubouchi, Sodegaura (JP);
Sumihiro Oda, Sodegaura (JP);
Hidetoshi Koga, Ichihara (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 221 days.

(21) Appl. No.: 13/811,042

(22) PCT Filed: Jul. 20, 2011

(86) PCT No.: PCT/JP2011/066439
§ 371 (c)(1),
(2), (4) Date: Jan. 18, 2013

(87) PCT Pub. No.: WO2012/011492
PCT Pub. Date: Jan. 26, 2012

(65) Prior Publication Data
US 2013/0123553 A1   May 16, 2013

(30) Foreign Application Priority Data

Jul. 20, 2010 (JP) ................. 2010-163037
Sep. 15, 2010 (JP) ................. 2010-206399

(51) Int. Cl.

| | | |
|---|---|---|
| C10L 1/16 | (2006.01) | |
| C10M 107/00 | (2006.01) | |
| C07C 13/615 | (2006.01) | |
| C07C 13/32 | (2006.01) | |
| C10M 127/02 | (2006.01) | |
| C10M 159/02 | (2006.01) | |
| C10M 105/04 | (2006.01) | |
| C10M 171/00 | (2006.01) | |
| C10M 171/02 | (2006.01) | |

(52) U.S. Cl.
CPC .............. C07C 13/32 (2013.01); C10M 105/04 (2013.01); C10M 127/02 (2013.01); C10M 159/02 (2013.01); C10M 171/002 (2013.01); C10M 171/02 (2013.01); C10M 2203/024 (2013.01); C10M 2203/045 (2013.01); C10N 2220/022 (2013.01); C10N 2220/026 (2013.01); C10N 2220/032 (2013.01); C10N 2230/02 (2013.01); C10N 2230/06 (2013.01); C10N 2230/10 (2013.01); C10N 2240/045 (2013.01); C10N 2240/201 (2013.01)

(58) Field of Classification Search
CPC ..... C10M 3/00; C07C 2102/42; C07C 13/605
USPC ........................ 508/200; 585/7, 22
See application file for complete search history.

(56) References Cited

U.S. PATENT DOCUMENTS

2007/0042915 A1   2/2007  Yoshida et al.
2010/0179079 A1*  7/2010  Sekiguchi et al. ............ 508/110

FOREIGN PATENT DOCUMENTS

| CN | 1863894 A | 11/2006 |
|---|---|---|
| CN | 101688141 A | 3/2010 |
| EP | 0 082 967 A2 | 7/1983 |
| EP | 0 082 967 A3 | 7/1983 |
| EP | 82967 A2 * | 7/1983 |
| EP | 1 672 050 A1 | 6/2006 |
| EP | A 672 050 A8 | 6/2006 |
| EP | 2 163 601 A1 | 3/2010 |
| JP | 58 154799 | 9/1983 |
| JP | 10 53780 | 2/1998 |
| JP | 2005 035699 | 4/2005 |
| JP | 2008 260951 | 10/2008 |
| JP | 2009 1756 | 1/2009 |
| WO | 03 014268 | 2/2003 |

OTHER PUBLICATIONS

Combined Chinese Office Action and Search Report issued Jan. 27, 2014 in Patent Application No. 201180035355.9 (with partial English language translation and English translation of categories of cited documents).
Extended European Search Report issued Oct. 27, 2014 in Patent Application No. 11809662.7.
N. Mason Joye Jr., et al., "Separation of Longifolene from Pine Oil," Journal of Chemical and Engineering Data, vol. 16, No. 3, XP055146763, Jul. 1971, pp. 366-367.
International Search Report Issued Oct. 25, 2011 in PCT/JP11/66439 Filed Jul. 20, 2011.

* cited by examiner

*Primary Examiner* — Vishal Vasisth
(74) *Attorney, Agent, or Firm* — Oblon, McClelland, Maier & Neustadt, L.L.P.

(57) ABSTRACT

A lubricating oil composition of the invention contains longifolene represented by the following formula (1), that is, (1S,3aR,4S,8aS)-4,8,8-trimethyl-9-methylene-decahydro-1,4-methanoazulene.

(1)

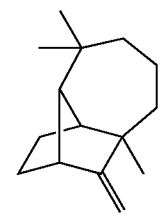

19 Claims, No Drawings

LUBRICATING OIL COMPOSITION AND LUBRICATING OIL COMPOSITION FOR CONTINUOUSLY VARIABLE TRANSMISSION

CROSS REFERENCE TO RELATED APPLICATIONS

This application is a 371 of PCT/JP2011/066439, filed Jul. 20, 2011.

The present application is a 35 U.S.C. §371 national stage patent application of International patent application PCT/JP2011/066439, filed on Jul. 20, 2011, published as WO/2012/011492 on Jan. 26, 2012, the text of which is incorporated by reference, and claims the benefit of the filing date of Japanese applications no. 2010-163037, filed on Jul. 2, 2010, and no. 2010-206399, filed on Sep. 15, 2010, the text of which applications is also incorporated by reference.

TECHNICAL FIELD

The present invention relates to a lubricating oil composition and a lubricating oil composition for a continuously variable transmission.

BACKGROUND ART

A lot of carbon materials derived from petroleum resources are still used today. However, exhaustion of the resources is becoming reality and novel carbon materials different from those derived from petroleum resources have been demanded. As an example of the novel carbon materials, an attempt has been made to use oils and fats and essential oils which are derived from natural plants, as a lubricating oil.

For instance, plant-derived fats and oils representative of soybean oil, wood oil, palm oil and the like can be obtained by expressing and extracting plants to provide crude oil and purifying the crude oil by distillation and the like. The plant-derived fats and oils are saturated or unsaturated fatty acid triglyceride and used in various fields such as cooking, fuels, medicine and lubricating oils. Moreover, an attempt to obtain a lubricating base oil exhibiting excellent low-temperature fluidity, oxidation stability and lubricity from the above plant-derived oils and fats according to an ester exchange method is also disclosed (see Patent Literature 1).

The plant-derived essential oils contain alcohols, aldehydes, ketones, esters, phenols, hydrocarbons and the like as components. Hydrocarbons are exemplified by terpenes and sesquiterpenes. Known examples of terpenes include: chain terpenes such as alloocimene, ocimene, myrcene and dihydromyrcene; and cyclic terpenes such as α-pinene, β-pinene, limonene, camphene, α-phellandrene, terpinene, terpinolene and 3-carene. Terpenes, which are often used in perfumes, are hydrocarbons having a molecular formula of $C_{10}H_{16}$. Since terpenes exhibit low viscosity, low flash point and the like although having high hydrolytic stability and volume resistivity, terpenes are not suitable for using as lubricating oils. Known examples of sesquiterpenes include: chain sesquiterpenes such as farnesene; and cyclic sesquiterpenes such as cedrene, β-caryophyllene, cadinene, valencene, Thujopsis and Guaiene. Sesquiterpenes are hydrocarbons having a molecular formula of $C_{15}H_{24}$. Since sesquiterpenes exhibit a high hydrolytic stability, a high volume resistivity, and further suitable viscosity and flash point, sesquiterpenes are usable as a low-viscous material for a lubricating oil.

In recent years, fuel efficiency regulations have been reinforced in each country because of growing awareness of environmental problems. In order to respond to such growing needs to improve a fuel efficiency, a continuously variable transmission (hereinafter, also referred to as CVT) tends to be employed. Since a speed is continuously variable in CVT, the most suitable engine speed can be selected corresponding to required output torque, resulting in a large improvement in the fuel efficiency. Moreover, since the engine speed is variable without a shock and is free from a fall in elevating a shift in CVT, an acceleration performance is improved and drivability is excellent. CVT is exemplified by a metal belt type CVT, a chain type CVT and a traction drive type CVT, each of which requires a high transmission efficiency. Accordingly, it is required to improve a transmission efficiency by developing a lubricating oil having a high traction coefficient. Above all, the traction drive type CVT is the most suitable for a high-class car since the traction drive type CVT transmits power through an oil film to make less noise.

On the other hand, since a lubricating oil for a continuously variable transmission is for transmitting power from a driving section to a driven section through an oil film, a higher traction coefficient of the lubricating oil results in a higher transmission efficiency. Accordingly, the traction coefficient is desired to be sufficiently large during an actual use.

Particularly, since the lubricating oil for the traction drive type CVT also serves as a typical lubricating oil in CVT, the lubricating oil for the traction drive type CVT needs to have a high viscosity enough to retain a sufficient oil film even at high temperatures for prevention of friction wear.

On the other hand, the lubricating oil for the traction drive type CVT needs to have a low viscosity at low temperatures (i.e., low-temperature fluidity) for a low-temperature starting performance in cold areas such as North America and North Europe. Accordingly, the lubricating oil for the traction drive type CVT requires a low dependency of a viscosity on temperatures, that is, a high viscosity index. In order to respond to such a demand, as shown in, for instance, Patent Literature 2, fluid for traction drive type CVT having a viscosity index of at least zero and containing a bicyclo[2.2.1]heptane derivative has been developed.

CITATION LIST

Patent Literature(s)

Patent Literature 1: JP-A-10-53780
Patent Literature 2: JP-A-2008-260951

SUMMARY OF THE INVENTION

Problems to be Solved by the Invention

The above plant-derived oils and fats is susceptible to hydrolysis as esters and exhibit a low volume resistivity also as polar substances. Accordingly, the plant-derived oils and fats cannot be used in a field requiring insulation. Moreover, most of the plant-derived oils and fats have an unsaturated fatty acid and exhibit a low oxidation stability. Further, since the plant-derived oils and fats exhibit a high pour point of −5 degrees C. to the room temperature although exhibiting a high viscosity index, the plant-derived oils and fats cannot be used in low temperature environments. These disadvantages are not changeable even by using the ester exchange method as shown in Patent Literature 1. Moreover, since sesquiterpenes as a plant-derived essential oil are hydrocarbons having unsaturated bonds, oxidation stability is low.

It cannot be said that the fluid for the traction drive type CVT disclosed in Patent Literature 2 exhibits a sufficient low-temperature startability. In addition, the traction coefficient is not always satisfactory as a lubricating oil for the traction drive type CVT.

An object of the invention is to provide a lubricating oil composition exhibiting a low pour point, a high viscosity index, a high oxidation stability, a high hydrolysis resistance and a high volume resistivity. Another object of the invention is to provide a lubricating oil composition for a continuously variable transmission exhibiting a high traction coefficient at high temperatures and an excellent low-temperature fluidity and capable of retaining an oil film at high temperatures.

Means for Solving the Problems

Inventors found that longifolene (one of cyclic sesquiterpene hydrocarbons) contained in an essential oil obtained from cypress, pine and the like exhibits a high hydrolytic stability, a high volume resistivity, and further suitable viscosity and flash point, so that longifolene is usable as a low-viscous base material for a lubricating oil. Further, since longifolene is structured to have an olefin at a terminal with a bulky substituent, longifolene exhibits a high oxidation stability. The invention has been completed based on this finding.

Specifically, the invention provides a lubricating oil composition and a lubricating oil composition for a continuously variable transmission as follows:
(1) a lubricating oil composition according to an aspect of the invention, containing longifolene;
(2) In the lubricating oil composition according to the above aspect of the invention, a content of the longifolene is at least 60 mass % of a total amount of the composition;
(3) the lubricating oil composition according to the above aspect of the invention, further comprising at most 5 mass % of β-caryophyllene;
(4) a lubricating oil composition for a continuously variable transmission according to another aspect of the invention, containing longifolene;
(5) the lubricating oil composition for the continuously variable transmission according to the above aspect of the invention, further containing bicyclo[2.2.1]heptane dimer
(6) In the lubricating oil composition for the continuously variable transmission according to the above aspect of the invention, the longifolene has a purity of at least 80%;
(7) the lubricating oil composition for the continuously variable transmission according to the above aspect of the invention, further containing at most 1 mass % of β-caryophyllene; and
(8) In the lubricating oil composition for the continuously variable transmission according to the above aspect of the invention, the composition is used as fluid for a traction drive type continuously variable transmission.

Advantages of the Invention

Since containing longifolene, the lubricating oil composition of the invention exhibits a low pour point, a high viscosity index, a high oxidation stability, a high hydrolysis resistance and a high volume resistivity.

Moreover, since containing longifolene, the lubricating oil composition for a continuously variable transmission of the invention exhibits a high traction coefficient, an excellent low-temperature fluidity and a high viscosity index for an oil film retainable at high temperatures.

DESCRIPTION OF EMBODIMENT(S)

A lubricating oil composition according to an aspect of the invention contains longifolene. A lubricating oil composition for a continuously variable transmission according to another aspect of the invention contains longifolene. In short, the invention provides a lubricating oil composition containing longifolene. Herein, longifolene is (1S,3aR,4S,8aS)-4,8,8-trimethyl-9-methylene-decahydro-1,4-methanoazulene, specifically, a compound having a structure represented by the following formula (1).

[Formula 1]

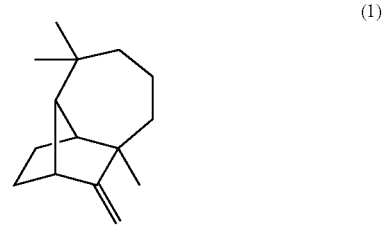

(1)

Longifolene is contained in an essential oil of pine or cypress. Longifolene having a high purity (60-90% purity) is easily obtainable by purifying the essential oil. The purified longifolene is usable as a lubricating oil, and also usable as a base oil for a lubricating oil. Use of longifolene as a base oil provides a lubricating oil composition exhibiting a low pour point, a high viscosity index, a high oxidation stability, a high hydrolysis resistance and a high volume resistivity. Moreover, since longifolene has an appropriate viscosity, lubricity of the lubricating oil composition is also excellent. A purity of longifolene is preferably at least 80%, more preferably at least 90%. Since the lubricating oil composition exhibits a higher viscosity index and more excellent oxidation stability as the purity of longifolene becomes higher, a higher purity of longifolene is preferable in the invention.

The lubricating oil composition according to the aspect of the invention and the lubricating oil composition for a continuously variable transmission according to the another aspect of the invention may contain a base oil other than longifolene described above. In order to provide advantages as the lubricating oil composition according to the aspect of the invention, a content of longifolene in the composition is preferably at least 60 mass %, more preferably at least 70 mass %, further preferably at least 80 mass %, particularly preferably at least 90 mass %. In order to provide advantages as the lubricating oil composition for a continuously variable transmission according to the another aspect of the invention, a content of longifolene is preferably at least 5 mass % based on a total amount of the composition, more preferably at least 10 mass %.

In the lubricating oil composition according to the aspect of the invention, the base oil other than longifolene may be selected from, for instance, mineral oil and synthetic oil as needed.

Examples of the mineral oil include: distillate oil obtained by distilling paraffin base crude oil, intermediate base crude oil or naphthene base crude oil at an ordinary pressure or distilling ordinary-pressure-distillation residue oil under diminished pressure; and refined oil obtained by refining the distilled oil in accordance with ordinary method, which specifically includes solvent refined oil, hydrogenated refined oil, dewaxing treated oil and white clay treated oil.

Examples of the synthetic oil include: low-molecular-weight polybutene; low-molecular-weight polypropylene; α-olefin oligomers having 8 to 14 carbon atoms and hydride thereof; ester compounds such as polyol esters (e.g. fatty acid esters of trimethylolpropane and fatty acid esters of pentaerythritol), diacid esters, aromatic polycarboxylic esters (e.g. trimellitic esters and pyromellitic esters) and ester phosphates; alkylaromatic compounds such as alkylbenzene and alkylnaphthalene; silicone oil; and fluorine oil (e.g. fluorocarbon and perfluoropolyether).

One of the base oils may be used alone or two or more of the base oils may be used in combination.

In the lubricating oil composition for a continuously variable transmission according to the another aspect of the invention, the base oil other than longifolene is particularly preferably a synthetic oil, further preferably a bicyclo[2.2.1] dimer, among which a bicyclo[2.2.1]heptane dimer represented by the following formula (2) is particularly preferable.

[Formula 2]

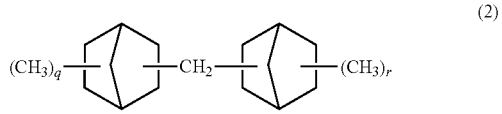

(2)

In the formula, q and r represent an integer of 1 to 5.

The bicyclo[2.2.1]heptane dimer represented by the formula (2) is more preferably endo-2-methyl-exo-3-methyl-exo-2-[(exo-3-methylbicyclo[2.2.1]hepto-exo-2-yl)methyl] bicyclo[2.2.1]heptane represented by the formula (3), or endo-2-methyl-exo-3-methyl-exo-2-[(endo-3-methylbicyclo [2.2.1]hepto-endo-2-yl)methyl]bicyclo[2.2.1]heptane represented by the formula (4).

[Formula 3]

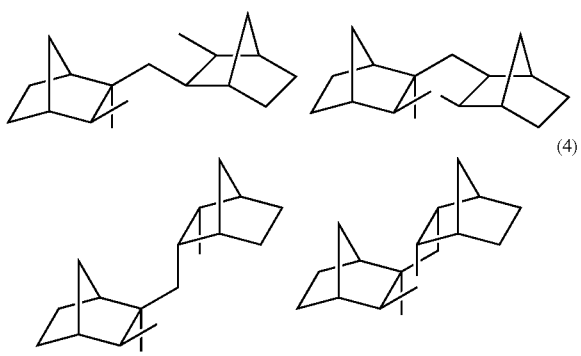

(3)

(4)

On the other hand, longifolene obtained from the essential oil of pine or cypress contains β-caryophyllene as an impure substance. Since β-caryophyllene exhibits a low viscosity index and a poor oxidation stability, a smaller content of β-caryophyllene is preferable. β-caryophyllene is (1R,4E, 9S)-4,11,11-trimethyl-8-methylene-bicyclo[7.2.0]undec-4-ene, specifically, a compound having the following structure.

[Formula 4]

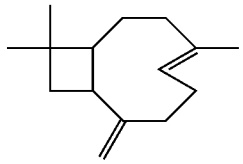

When β-caryophyllene is present in the lubricating oil composition, oxidation stability may be impaired, and further, may adversely affect the viscosity index. Accordingly, in the lubricating oil composition according to the aspect of the invention, a content of β-caryophyllene is preferably at most 5 mass % based on the total amount of the composition, more preferably at most 3 mass %. Moreover, in the lubricating oil composition for a continuously variable transmission according to the another aspect of the invention, the content of β-caryophyllene is preferably at most 1 mass % based on the total amount of the composition.

The lubricating oil composition according to the aspect of the invention and the lubricating oil composition for a continuously variable transmission according to the another aspect of the invention may contain a predetermined additive. Examples of the additive include an antioxidant, oiliness agent, extreme pressure agent, detergent dispersant, viscosity index improver, rust inhibitor, metal deactivator and antifoaming agent. One of the additives may be used alone or two or more of the additives may be used in combination.

Examples of the antioxidant to be used include an aminic antioxidant, phenolic antioxidant, phosphorous antioxidant and sulfuric antioxidant, which are used in a typical hydrocarbon lubricating oil. One of the antioxidants may be used alone or two or more of the antioxidants may be used in combination.

Examples of the aminic antioxidant include: monoalkyldiphenylamine compounds such as monooctyldiphenylamine and monononyldiphenylamine; dialkyl diphenylamine compounds such as 4,4'-dibutyldiphenylamine, 4,4'-dipentyldiphenylamine, 4,4'-dihexyldiphenylamine, 4,4'-diheptyldiphenylamine, 4,4'-dioctyldiphenylamine and 4,4'-dinonyldiphenylamine; polyalkyldiphenylamine compounds such as tetrabutyldiphenylamine, tetrahexyldiphenylamine, tetraoctyldiphenylamine and tetranonyldiphenylamine; and naphthylamine compounds such as alpha-naphthylamine, phenyl-alpha-naphthylamine, butylphenyl-alpha-naphthylamine, pentylphenyl-alpha-naphthylamine, hexylphenyl-alpha-naphthylamine, heptylphenyl-alpha-naphthylamine, octylphenyl-alpha-naphthylamine and nonylphenyl-alpha-naphthylamine.

Examples of the phenolic antioxidant include: monophenol compounds such as 2,6-di-tert-butyl-4-methylphenol and 2,6-di-tert-butyl-4-ethylphenol; and diphenol compounds such as 4,4'-methylenebis(2,6-di-tert-butylphenol) and 2,2'-methylenebis(4-ethyl-6-tert-butylphenol).

Examples of the phosphorous antioxidant include triphenyl phosphite and diethyl[3,5-bis(1,1-dimethylethyl)-4-hydroxyphenyl]methyl]phosphonate.

Examples of the sulfuric antioxidant include: thioterpene compounds such as 2,6-di-tert-butyl-4-(4,6-bis(octylthio)-1, 3,5-triazine-2-ylamino)phenol and a reactant of phosphorus pentasulfide and pinene; and dialkyl thiodipropionate such as dilauryl thiodipropionate and distearyl thiodipropionate.

In the lubricating oil composition according to the aspect of the invention, a content of the antioxidant is typically in a range of 0.01 mass % to 10 mass % based on the total amount of the composition, preferably 0.03 mass % to 5 mass %. In the lubricating oil composition for a continuously variable transmission according to the another aspect of the invention, the antioxidant may be added at a minimum content necessary to keep oxidation stability. Since the traction coefficient at high temperatures is decreased as the added antioxidant is increased, the smaller content of the antioxidant is better. The content of the antioxidant is preferably in a range of 0.01 mass % to 1 mass % based on the total amount of the composition.

Examples of the oiliness agent include: aliphatic alcohols; fatty acid compounds such as fatty acids and fatty acid metal salts; ester compounds such as polyol esters, sorbitan esters and glycerides; and amine compounds such as aliphatic amines. A content of the oiliness agent is typically in a range of 0.1 mass % to 30 mass % based on the total amount of the composition, preferably in a range of 0.5 mass % to 10 mass %, in terms of blending effects.

Examples of the extreme pressure agent include a sulfur extreme pressure agent, a phosphorus extreme pressure agent, an extreme pressure agent containing sulfur and metal and an extreme pressure agent containing phosphorus and metal. One of the extreme pressure agents may be used alone, or two or more of the extreme pressure agents may be used in combination. Any extreme pressure agent may be used as long as containing at least one of sulfur atom and phosphorous atom in a molecule and exhibiting load bearing properties and wear resistance. Examples of the extreme pressure agent containing sulfur in a molecule include sulfurized fats and oils, sulfurized fatty acids, ester sulfide, olefin sulfide, dihydrocarbyl polysulfide, thiadiazole compounds, alkylthiocarbamoyl compounds, triazine compounds, thioterpene compounds and dialkylthiodipropionate compounds.

Representative examples of the extreme pressure agent containing phosphorous in a molecule include phosphates such as tricresyl phosphate and amine salts thereof.

Examples of the extreme pressure agent containing sulfur, phosphorous and metal include: zinc dialkylthiocarbamate (Zn-DTC), molybdenum dialkylthiocarbamate (Mo-DTC), lead dialkylthiocarbamate, tin dialkylthiocarbamate, zinc dialkyldithiocarbamate (Zn-DTP), molybdenum dialkyldithiophosphate (Mo-DTP), sodium sulfonate, and calcium sulfonate. Representative examples of the extreme pressure agent containing phosphorous in a molecule include phosphates such as tricresyl phosphate and amine salts thereof. A content of the extreme pressure agent is typically in a range of 0.01 mass % to 30 mass % based on the total amount of the composition, preferably in a range of 0.01 mass % to 10 mass %, in terms of the blending effects and economical efficiency.

Examples of the detergent dispersant include metal sulfonates, metal salicylates, metal phenates, and succinimide. A content of the detergent dispersant is typically in a range of 0.1 mass % to 30 mass % based on the total amount of the composition, preferably in a range of 0.5 mass % to 10 mass %, in terms of the blending effects.

Examples of the viscosity index improver include polymethacrylates, dispersed polymethacrylates, olefin copolymers (e.g. ethylene-propylene copolymers), dispersive olefin copolymers, and styrene copolymers (e.g. hydrogenated styrene-diene copolymers). In the lubricating oil composition according to the aspect of the invention, a content of the viscosity index improver is typically in a range of 0.5 mass % to 35 mass % based on the total amount of the composition, preferably 1 mass % to 15 mass %, in terms of the blending effects. In the lubricating oil composition for a continuously variable transmission according to the another aspect of the invention, the viscosity index improver only needs to be added so that a viscosity at 100 degrees C. is at least 5 mm$^2$/s. When the viscosity index improver is excessively added, the traction coefficient of the composition is decreased and a low-temperature viscosity thereof is increased. Accordingly, the viscosity index improver is preferably in a range of 0.3 mass % to 5 mass % based on the total amount of the composition.

Examples of the rust inhibitor include alkanolamines such as metal sulfonates, succinic acid esters, alkylamines and monoisopropanolamines. A content of the rust inhibitor is typically in a range of 0.01 mass % to 10 mass % based on the total amount of the composition, preferably in a range of 0.05 mass % to 5 mass %, in terms of the blending effects.

Examples of the metal deactivator include benzotriazole and thiadiazole. A content of the metal deactivator is typically preferably in a range of 0.01 mass % to 10 mass % based on the total amount of the composition, preferably in a range of 0.01 mass % to 1 mass %, in terms of the blending effects.

Examples of the antifoaming agent include methylsilicone oil, fluorosilicone oil, and polyacrylates. A content of the antifoaming agent is typically about 0.0005 to 0.01 mass % based on the total amount of the composition, in terms of the blending effects.

The lubricating oil composition according to the aspect of the invention is usable in various applications such as an internal combustion engine, fluid coupling, slide bearing, ball bearing, oil-impregnated bearing, fluid dynamic bearing, compression device, chain, gear, hydraulic device, timepiece component, hard disc, freezer, cutting, rolling, squeezing drawing, form rolling, forging, heat-treating, heat medium, cooling agent, coolant, washing, shock absorber, rust inhibition, brake and sealing device. The lubricating oil composition for a continuously variable transmission according to the another aspect of the invention is required to have a high transmission efficiency and is usable as a lubricating oil composition for a continuously variable transmission such as a metallic belt type, chain type, and traction drive type ones in which a lubricating oil having a high traction coefficient is required. Since the lubricating oil composition has a high viscosity enough to retain a sufficient oil film even at high temperatures, the lubricating oil composition is suitably usable particularly as a traction drive fluid that transmits power through an oil film.

EXAMPLES

Next, a lubricating oil composition of the invention will be described in more details with reference to Examples 1 and 2 and Comparative 1 and a lubricating oil composition for a continuously variable transmission of the invention will be described in more details with reference to Examples 3 and 4 and Comparatives 2 and 3. However, the invention shall by no means be limited to Examples and Comparatives. Specifically, sample oils were prepared as described below and evaluated.

Example 1

Longifolene having a purity of 80% (manufactured by Honghe Fine Chemical Co., Ltd) was purified and distilled in a 120-cm column with a 40-mm diameter which was filled with a filler to obtain (1S,3aR,4S,8aS)-4,8,8-trimethyl-9-methylenedecahydro-1,4-methanoazulene having a purity of 90% (a fraction having a boiling point of 145 to 149 degrees C. at 30 mmHg) at a yield of 70%. This fraction was used as a sample oil. Note that the fraction contained 2.9 mass % of β-caryophyllene.

Example 2

Longifolene having a purity of 60% (manufactured by YASUHARA CHEMICAL CO., LTD.) was used as a sample oil. The longifolene contained 14.4 mass % of β-caryophyllene.

Comparative 1

A plant-derived oil and fat (commercially available soybean oil) was used as a sample oil.

Measurement Method of Properties of Sample Oils

Various properties of the above-described sample oils were measured according to the following methods. Results are shown in Table 1.

(1) Kinematic Viscosity

Kinematic viscosities at 40 degrees C. and 100 degrees C. were measured according to JIS K 2283.

(2) Viscosity Index

A viscosity index was measured according to JIS K 2283.

(3) Density at 15 degrees C.

A density at 15 degrees C. was measured according to JIS K 2249.

(4) Pour Point

A pour point was measured according to JIS K 2269.

(5) Volume Resistivity

A volume resistivity was measured according to JIS C 2101.

(6) RBOT Lifetime 0.5 mass % of 2,6-di-tert-butyl-4-methylphenol was added to each of the above sample oils. In each of the sample oils, time (minutes) elapsed before pressure reduction was terminated was measured according to JIS K 2514.

TABLE 1

| | Example 1 90%-longifolene | Example 2 60%-longifolene | Comparative 1 |
|---|---|---|---|
| β-caryophyllene content (mass %) | 2.9 | 14.4 | — |
| Kinematic Viscosity at 40° C. (mm²/s) | 7.588 | 7.368 | 31.85 |
| Kinematic Viscosity at 100° C. (mm²/s) | 2.383 | 2.102 | 7.670 |
| Viscosity Index | 144 | 74 | 224 |
| Density at 15° C. (g/cm³) | 0.9396 | 0.9380 | 0.9227 |
| Pour Point (° C.) | <−50 | <−50 | −2 |
| Volume Resistivity (Ω·cm) | $1 \times 10^{14}$ | $6 \times 10^{12}$ | $5 \times 10^{11}$ |
| RBOT Lifetime (150° C.) (min.) | 96 | 32 | 18 |

Evaluation Results

It was recognized that the pour point of each of the sample oils in Examples was lower than that of the sample oil (soybean oil) in Comparative, resulting in a favorable low-temperature fluidity. It was also recognized that the sample oils in Examples had a favorable hydrolysis resistance since the sample oils in Examples were hydrocarbon compounds, not the ester compound as in Comparative.

It was recognized that the sample oil containing a small content of β-caryophyllene in Example 1 had a long remaining time of RBOT, a favorable oxidation stability, and a long lifetime as a lubricating oil. Moreover, since the sample oil containing the small content of β-caryophyllene in Example 1 had a high volume resistivity, the sample oil is suitable for such an application as requires insulation. Further, it was recognized that, since the sample oil containing the small content of β-caryophyllene in Example 1 had a high viscosity index, the sample oil had a low dependency of the viscosity on the temperatures and was suitable as a lubricating oil. It was recognized that the sample oil containing the small content of β-caryophyllene in Example 1 had an extremely favorable oxidation stability and an extremely long lifetime as a lubricating oil.

Next, the lubricating oil composition of a continuously variable transmission of the invention will be described in more details with reference to Examples 3 and 4 and Comparatives 2 and 3.

Manufacturing Example 1

Preparation of Hydrogenated Bicyclo[2.2.1]Heptane Dimer (Fluid 1)

(1) Preparation of Material Olefin

A two-liter stainless steel-made autoclave was charged with 561 g (8 mol) of crotonaldehyde and 352 g (2.67 mol) of dicyclopentadiene. The mixture was reacted at 170 degrees C. for three hours with stirring.

The reaction solution was cooled down to the room temperature, and then 18 g of a sponge nickel catalyst (M-300T, manufactured by Kawaken Fine Chemicals Co., Ltd.) was added thereto to carry out hydrogenation reaction at a hydrogen pressure of 0.9 MPa·G and a reaction temperature of 150 degrees C. for four hours. After the reaction solution was cooled down, the catalyst was separated by filtration, and then filtrate was distilled under reduced pressure to obtain 565 g of a 105 degrees C./2.66 kPa fraction. This fraction was analyzed by a mass spectrum and a nuclear magnetic resonance spectrum. As a result, it was observed that the above fraction was 2-hydroxymethyl-3-methylbicyclo[2.2.1]heptane and 3-hydroxymethyl-2-methylbicyclo[2.2.1]heptane. Next, a quartz glass-made flow atmospheric reaction tube having a 20-mm outer diameter and a 500-mm length was charged with 20 g of γ-alumina (N612N, manufactured by Nikki Chemical Co., Ltd.) to carry out dehydration reaction at a reaction temperature of 285 degrees C. and a mass space velocity (WHSV) of 1.1 hr⁻¹ to obtain 490 g of a dehydration reaction product of 2-hydroxymethyl-3-methylbicyclo[2.2.1]heptane and 3-hydroxymethyl-2-methylbicyclo[2.2.1]heptane which contains 55 mass % of 2-methylene-3-methylbicyclo[2.2.1]heptane and 3-methylene-2-methylbicyclo[2.2.1]heptane and 30 mass % of 2,3-dimethylbicyclo[2.2.1]hepto-2-ene.

(2) Preparation of Dimer

A one-liter four-neck flask was charged with 8 g of a boron trifluoride diethyl ether complex and 400 g of the olefin compound obtained in the above (1) to carry out dimerization reaction at zero degrees C. for six hours with stirring using a mechanical stirrer. This reaction mixture was washed with a diluted NaOH aqueous solution and a saturated saline solution to obtain an olefin compound.

(3) Hydrogenation Step

A one-liter autoclave was charged with 300 g of the olefin compound obtained in the above (2) and 12 g of a nickel/diatomaceous earth catalyst for hydrogenation (N-113, manufactured by Nikki Chemical Co., Ltd.) to carry out hydrogenation reaction at a hydrogen pressure of 3 MPa·G and a reaction temperature of 80 degrees C. for five hours, then further at the reaction temperature of 180 degrees C. for four hours. After finishing the reaction, the catalyst was separated by filtration and the filtrate was distilled under reduced pressure to obtain 240 g of a targeted hydrogenated dimer. The obtained fluid was defined as Fluid 1

Example 3

Preparation of Longifolene (Fluid 2)

Longifolene having a purity of 80% (manufactured by Honghe Fine Chemical Co., Ltd) was purified and distilled in a 120-cm column with a 40-mm diameter which was filled with a filler to obtain 4,8,8-trimethyl-9-methylenedecahydro-1,4-methanoazulene having a purity of 90% (a fraction having a boiling point of 145 to 149 degrees C. at 30 mmHg) at a yield of 70%. The obtained fluid was defined as Fluid 2

Example 4

85 mass % of Fluid 1 in Manufacturing Example 1 and 15 mass % in Fluid 2 of Example 3 were mixed to provide Fluid 3.

Manufacturing Example 2

Synthesis of Fluid 4

A hydrogenated linear dimer of α-methylstyrene was synthesized according to a method disclosed in International Publication WO2003/014268.

A 500-ml four-neck flask equipped with a reflux condenser, a stirring device and a thermometer was charged with 4 g of activated clay (Galleon Earth NS, manufactured by Mizusawa Industrial Chemical. Ltd.), 10 g of diethylene glycol monomethyl ether and 200 g of α-methylstyrene, and the mixture was heated at a reaction temperature of 105 degrees C. and stirred for four hours. After finishing the reaction, the obtained liquid was analyzed by a gas chromatography to find that a conversion rate was 70%, a selectivity of the target product (a linear dimer of α-methylstyrene) was 95%, a selectivity of a byproduct (a cyclic dimer of α-methylstyrene) was 1%, and a selectivity of a substance having a high boiling point such as a trimer was 4%. This reaction mixture was added into a one-liter autoclave with 15 g of a nickel/diatomaceous earth catalyst for hydrogenation (N-113, manufactured by Nikki Chemical Co., Ltd.) to carry out hydrogenation reaction (hydrogen pressure: 3 MPa·G, reaction temperature: 250 degrees C., reaction time: five hours). The reactant was separated by filtration, concentrated and then distilled under reduced pressure to obtain 125 g of a hydrogenated linear dimer of α-methylstyrene (i.e., 2,4-dicyclohexyl-2-methylpentane) having a purity of 99% (Fluid 4).

Comparative 2

Synthesis of Hydrogenated Cyclooctene Dimer (Fluid 5)

A hydrogenated cyclooctene dimer was synthesized according to a method disclosed in Example 13 of Patent Literature 1 (JP-A-2008-260951).

A one-liter four-neck flask was charge with 100 g of a boron trifluoride 1.5 water complex and 200 ml of heptane, and 450 g of cyclooctene was dropped thereto at 20 degrees C. for four hours with stirring for dimerization reaction.

This reaction mixture was washed with a diluted NaOH aqueous solution and a saturated saline solution, and heptane was distilled therefrom. Subsequently, the reaction mixture was added into a one-liter autoclave with 15 g of a nickel/diatomaceous earth catalyst for hydrogenation (N-113, manufactured by Nikki Chemical Co., Ltd.) to carry out hydrogenation reaction (hydrogen pressure: 3 MPa·G, reaction temperature: 200 degrees C., reaction time: three hours). After finishing the reaction, the catalyst was separated by filtration and the filtrate was distilled under reduced pressure to obtain 210 g of a targeted hydrogenated dimer (Fluid 5).

Comparative 3

Fluid 5 of Comparative 2 was mixed with Fluid 4 of Manufacturing Example 2 so that a content of Fluid 5 was 15 wt % of the entire fluid, whereby Fluid 6 was obtained.

Measurement Method of Properties of Sample Oils

Various properties of the above-described sample oils (Fluids 1 to 6) were measured according to the following methods. Results are shown in Table 1.

(1) Kinematic Viscosity

Kinematic viscosities at 40 degrees C. and 100 degrees C. were measured according to JIS K 2283.

(2) Viscosity Index

A viscosity index was measured according to JIS K 2283.

(3) Density at 15 degrees C.

A density at 15 degrees C. was measured according to JIS K 2249.

(4) Viscosity at −40 degrees C.

A viscosity at −40 degrees C. was measured according to ASTM D2983.

(5) Traction Coefficient

A traction coefficient at 120 degrees C. was measured by a dual cylindrical rolling sliding frictional test machine. Specifically, one of the same sized cylinders in contact (diameter: 52 mm, thickness: 6 mm, driven cylinder: a bulging cylinder having a curvature radius of 10 mm, driving cylinder: a right cylinder, i.e., no crowning) was driven at a constant speed while the other cylinder was rotated at continuously varied speed. A load of 98.0 N was applied to a contact part of both the cylinders by a spindle to measure a tangential force generated between both the cylinders, that is, the traction force, whereby the traction coefficient was determined. The cylinders were made of bearing steel SUJ-2 with a mirror finish and had an average circumferential velocity of 6.8 m/s and a maximum hertz contact pressure of 1.23 GPa. Moreover, in measuring the traction coefficient at a fluid temperature (oil temperature) of 120 degrees C., the oil temperature was raised from 40 degrees up to 140 degrees C. by heating an oil tank using a heater, whereby the traction coefficient at a slide-roll ratio of 5% was determined.

TABLE 2

|  | Manufacturing Example 1 Fluid 1 | Example 3 Fluid 2 | Example 4 Fluid 3 | Manufacturing Example 2 Fluid 4 | Comparative 2 Fluid 5 | Comparative 3 Fluid 6 |
| --- | --- | --- | --- | --- | --- | --- |
| Kinematic Viscosity at 40° C. (mm$^2$/s) | 27.97 | 7.588 | 22.13 | 20.23 | 7.817 | 17.18 |
| Kinematic Viscosity at 100° C. (mm$^2$/s) | 4.644 | 2.383 | 4.177 | 3.572 | 2.144 | 3.28 |
| Viscosity Index | 69 | 144 | 83 | 13 | 61 | 21 |
| Density at 15° C. (g/cm$^3$) | 0.9744 | 0.9396 | 0.9693 | 0.9009 | 0.8878 | 0.8989 |
| Viscosity at −40° C. (Pa · s) | 212 | 1> | 38 | 260 | 3 | 120 |
| Traction Coefficient at 120° C. | 0.097 | 0.077 | 0.092 | 0.082 | 0.061 | 0.074 |

Evaluation Results

The viscosity index and the traction coefficient of the sample oils in Examples 3 and 4 are larger than those of the sample oils in Comparatives 2 and 3. In comparison with Fluid 1 in Manufacturing Example 1 and Fluid 4 in Manufacturing Example 2, both of which contain no longifolene, Fluid 3 in Example 4 containing longifolene exhibits a significantly small viscosity at −40 degrees C. while keeping a large traction coefficient at 120 degrees C.

The invention claimed is:

1. A lubricating oil composition comprising:
   at least 5 mass % of longifolene based on a total amount of the composition; and
   greater than 0 mass % to 5 mass % of β-caryophyllene based on the total amount of the composition.
2. The lubricating oil composition of claim 1, comprising at least 60 mass % of the longifolene based on the total amount of the composition.
3. A method of lubricating a continuously variable transmission, comprising applying the lubricating oil composition of claim 1 to the continuously variable transmission.
4. The lubricating oil composition of claim 1, further comprising a bicyclo[2.2.1]heptane dimer.
5. The lubricating oil composition of claim 1, wherein the longifolene has a purity of at least 80%.
6. The lubricating oil composition of claim 1, comprising greater than 0 mass % to 1 mass % of the β-caryophyllene based on the total amount of the composition.
7. The method of claim 3, wherein the continuously variable transmission is a traction drive type continuously variable transmission.
8. The lubricating oil composition of claim 1, comprising at least 10 mass % of the longifolene based on the total amount of the composition.
9. The lubricating oil composition of claim 1, comprising at least 70 mass % of the longifolene based on the total amount of the composition.
10. The lubricating oil composition of claim 1, comprising at least 80 mass % of the longifolene based on the total amount of the composition.
11. The lubricating oil composition of claim 1, comprising at least 90 mass % of the longifolene based on the total amount of the composition.
12. The lubricating oil composition of claim 1, wherein the longifolene has a purity of at least 90%.
13. The lubricating oil composition of claim 1, further comprising greater than 0 mass % to 3 mass % of the β-caryophyllene based on the total amount of the composition.
14. The lubricating oil composition of claim 4, wherein the longifolene has a purity of at least 80%.
15. The lubricating oil composition of claim 4, comprising greater than 0 mass % to 1 mass % of the β-caryophyllene based on the total amount of the composition.
16. The lubricating oil composition of claim 1, wherein a viscosity of the composition at 100 degrees C. is at least 5 $mm^2/s$.
17. A method of lubricating a continuously variable transmission, comprising applying the lubricating oil composition of claim 4 to the continuously variable transmission.
18. A method of lubricating a continuously variable transmission, comprising applying the lubricating oil composition of claim 6 to the continuously variable transmission.
19. A method of lubricating a continuously variable transmission, comprising applying the lubricating oil composition of claim 15 to the continuously variable transmission.

* * * * *